United States Patent [19]
Zanzucchi

[11] Patent Number: 6,118,126
[45] Date of Patent: Sep. 12, 2000

[54] METHOD FOR ENHANCING FLUORESCENCE

[75] Inventor: Peter John Zanzucchi, Lawrenceville, N.J.

[73] Assignee: Sarnoff Corporation, Princeton, N.J.

[21] Appl. No.: 09/187,355

[22] Filed: Nov. 6, 1998

Related U.S. Application Data

[63] Continuation-in-part of application No. 08/961,860, Oct. 31, 1997.

[51] Int. Cl.⁷ .......................... G01N 21/64; G01N 33/58; G01N 33/543; G01N 33/545
[52] U.S. Cl. .................................... 250/458.1; 422/82.07; 422/82.08; 250/461.1; 250/461.2; 436/172; 436/518; 436/524; 436/531
[58] Field of Search ..................................... 436/172, 518, 436/524, 531; 422/82.07, 82.08; 250/458.1, 461.1, 461.2

[56] References Cited

U.S. PATENT DOCUMENTS

| | | | |
|---|---|---|---|
| 4,299,916 | 11/1981 | Litman et al. | 435/6 |
| 4,710,458 | 12/1987 | Maines | 435/12 |
| 4,740,459 | 4/1988 | Chen et al. | 435/18 |
| 4,824,776 | 4/1989 | Heller | 435/6 |
| 4,868,106 | 9/1989 | Ito et al. | 435/7 |
| 4,921,878 | 5/1990 | Rothman et al. | 521/53 |
| 4,996,143 | 2/1991 | Heller et al. | 435/6 |
| 5,011,769 | 4/1991 | Duck et al. | 435/6 |
| 5,232,830 | 8/1993 | Van Ness | 435/6 |
| 5,236,827 | 8/1993 | Sussman et al. | 435/34 |
| 5,340,716 | 8/1994 | Ullman et al. | 435/6 |
| 5,573,909 | 11/1996 | Singer et al. | 435/6 |
| 5,580,730 | 12/1996 | Okamoto | 435/6 |
| 5,605,761 | 2/1997 | Burns et al. | 428/412 |
| 5,643,730 | 7/1997 | Banker et al. | 435/6 |
| 5,654,418 | 8/1997 | Sheiness et al. | 536/24.32 |
| 5,695,930 | 12/1997 | Weinstein et al. | 435/5 |
| 5,705,600 | 1/1998 | Jones et al. | 528/298 |
| 5,714,380 | 2/1998 | Neri et al. | 435/287.2 |
| 5,776,785 | 7/1998 | Lin et al. | 436/527 |
| 5,861,270 | 1/1999 | Nelis | 435/34 |
| 5,897,811 | 5/1999 | Lesko | 252/301.35 |

FOREIGN PATENT DOCUMENTS

| | | |
|---|---|---|
| 91 12276 | 8/1991 | WIPO . |
| 97 27324 | 7/1997 | WIPO . |

OTHER PUBLICATIONS

L. Middendorf et al.: "A Two–Dimensional Infrared Flourescence Scanner Used for DNA Analysis", SPIE Proceedings, vol. 2388 (Advances in flourescence sensing technology), 1995. pp. 44–45, XP002099593, whole document.
A. Doningo et al.: "Visualization Under Ultraviolet Light Enhances 100–Fold the Sensitivity of Peroxidase Blots", Analytical Biochemistry, vol. 182, 1989, pp. 176–181, XP002099594 San Diego, US, the whole document.
K.A. O'Donnell et al., Experimental study of scattering from characterized random surfaces, J. Opt. Soc. Am. A/vol. 4, No. 7, pp. 1194–1205 (1987).
International Search Report for PCT 91 122 76 A for PCT 97 27324 A, for PCT/US/98/23184.
F.O. Glockner et al.: "An in Situa Hybridization Protocol for Detection and Identification of Planktonic Bacteria", Systematic and Applied Microbiology, vol. 19, 1996, pp. 403–406, XP002099592 Stuttgart, DE, the whole document.

*Primary Examiner*—Nita Minnifield
*Assistant Examiner*—Padma Baskar
*Attorney, Agent, or Firm*—William J. Burke

[57] ABSTRACT

The present invention relates to a method for the enhancement of fluorescence wherein a fluorophor is connected to a textured material. The method can be used in any forensic or medical diagnostic assay, particularly where the absence or presence of a molecule having a concentration of less than about 1 μg/ml is desirably determined.

13 Claims, 2 Drawing Sheets

METHOD FOR ENHANCING FLUORESCENCE

The present application is a continuation-in-part of U.S. application Ser. No. 08/961,860, filed Oct. 31, 1997, for Peter John Zanzucchi.

This invention was made with U.S. Government support under Contract No. 70NANB5H 1037-130-67-GRAN. The U.S. Government has certain rights in this invention.

The present invention relates to the field of molecular identification and, in particular, the use of a method for enhancing fluorescence of a fluorophor, particularly when such a fluorophor is attached to a molecular species of interest.

The amounts of material for clinical assays can vary over six to twelve orders of magnitude depending on the type of assay to be performed, the efficiency of the assay, the degree of chemical amplification in the assay and so forth. In a clinical assay for a particular sequence of DNA, for example, wherein the sequence is amplified using a conventional polymerase chain reaction (PCR) as known in the art, the range of concentration of resultant amplicons (i.e., the generated copies of the sequence of interest) may vary by more than six orders of magnitude. Where the sequence of interest is single copy, running a conventional PCR protocol can provide about a million copies, which, presuming an amplicon length of 200 base pairs, would constitute about a picogram ($10^{-12}$ grams). A high copy number sequence of interest, in contrast, can result in $10^{10}$ to $10^{12}$ copies after amplification, i.e., from nanogram to microgram quantities of amplified DNA. Thus, various DNA assays can require detection of material over six or more orders of magnitude. Similar issues exist for the detection of antibodies in immunoassays where broad ranges of antigen concentration are generally common to such clinical assays. Accordingly, sensitive detection methods with broad range of application are essential.

Whereas various non-radioactive methods of detecting DNA and other assay products exist, including via fluorescence and light or color generation methods, as reviewed by Kricka in *Nonisotopic DNA Probe Techniques* (Academic Press, Inc., San Diego, Calif., 1992), they are selected more for their relatively low cost of disposal as compared to the cost of disposal of isotopes. Indeed, it is the isotopic methods of detection that better address the problem posed by the large range of resultant concentrations of amplicons in the aforementioned PCR assay, however the use of isotopic detection methods is prohibitory due to regulations for shipment, storage, and disposal of these materials. Accordingly, a nonisotopic method of detecting a wide range of concentrations of an analyte would be desirable.

One such approach relies on the detection of fluorescent dyes that can selectively be attached to an analyte of interest. Fluorescence detection is dependent on the concentration of the fluorophor (i.e., the fluorescent dye), the path length between the source of fluorescent reaction and detector thereof, the absorptivity of the fluorophor, the incident laser intensity, and the fluorophor quantum yield. Such detection by fluorescence of biochemical material, such as the detection of fluorophor-labeled DNA, is well-known, albeit limited with respect to lower detection limits of about femtomoles of DNA, i.e., approximately $10^{-11}$ grams. It is desirable that such fluorescence detection provide for detection of even trace amounts of an analyte of interest, having concentrations of less than about attomoles ($10^{-18}$ moles) of DNA, e.g., approximately $10^{-14}$ grams.

SUMMARY OF THE INVENTION

In one embodiment, the invention relates to a method for enhancing fluorescence comprising contacting a fluorophor with a textured material, thereby forming a complex. In a second embodiment, the invention relates to a method for identifying an analyte comprising contacting the analyte with a binding species, wherein the binding species is connected to a fluorophor that is connected to or within a textured material.

More specifically, the invention provides a method for enhancing fluorescence comprising contacting a fluorophor with a textured material, thereby forming a complex, and detecting fluorophor complex-associated fluorescence, if present, on or in the textured material. In one preferred embodiment, the textured material is incorporated on a surface of a bead or a well of a multi-welled plate.

The method can comprise conducting an analytical reaction in a cassette or chip for conducting reaction processes, contacting a fluorophor-containing product of the reaction with the textured material, wherein the textured material is incorporated in a detection or reaction chamber of the cassette or chip, and detecting fluorescence from the textured material. Further, the method can comprise directing excitatory light to the textured surface at substantially a 90° incident angle, and collecting emissions located within a 20° cone surrounding the axis of reflection of the incident excitatory light.

In another preferred embodiment, the method can comprise conducting an analytical reaction in the presence of the textured material such that a substrate fluorophor remains in a liquid phase and product fluorophor associates with the textured substrate, wherein the analytical reaction does not substantially increase the fluorescence yield of the product fluorophor, and detecting fluorescence from the textured material by directing an excitatory light source through the liquid phase to the textured material. A "substantial increase" in the fluorescence yield due to the reaction (or reactions) refers an increase which would compete with the increase due to associating with the textured material to prevent reliable detection of that latter increase.

The invention further provides a device for conducting reactions comprising: a cassette or chip for conducting reaction processes comprising at least one detection or reaction chamber which contains a textured material that enhances the fluorescence of a fluorophor associated therewith; a source of light selected to emit light that is not absorbed by the textured material in an amount effective to diminish the fluorescence enhancement, which light source is aligned with the at least one detection or reaction chamber; and a detector aligned with an axis of reflectance from the textured substrate for the light emitted by the light source.

The invention also provides a device for conducting a fluorescence measurement comprising an textured material embossed to define a reaction well or chamber.

Definitions

Figure 1:
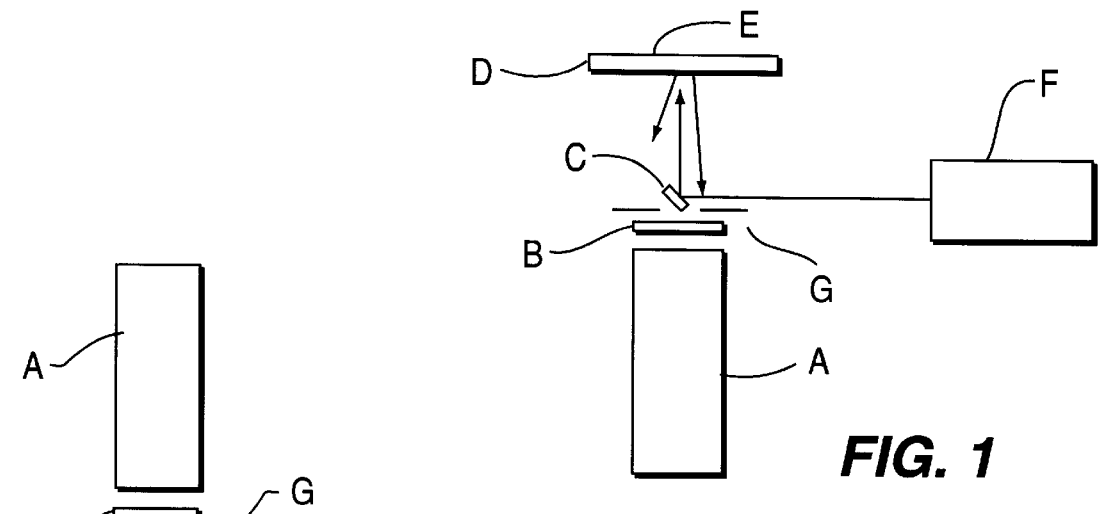
FIG. 1 displays a backscatter-mode enhanced fluorescence unit.

The following terms shall have, for the purposes of this application, the respective meanings set forth below. In particular, for the purpose of interpreting the claims, the term definitions shall control over any assertion of a contrary meaning based on other text found herein:

The modifier "about" is used herein to indicate that certain preferred operating ranges, such as ranges for pH, material amounts and temperature, are not fixedly determined. The meaning will often be apparent to one of ordinary skill. For example, a recitation of a temperature range of about 15° C. to about 40° C. in reference to, for example, a enzyme-driven reaction would be interpreted to include other to include like temperatures which can be expected to favor a useful catalysis rate for the enzyme, such as 11° C. or 44° C. However, other preferred ranges can also provide guidance such that, in the above example, a preferred range of 10° C. to 45° C., would indicate that the "about" temperatures falling within the included range should not fall closer than half way to the endpoint of the broader range. Where guidance from the experience of those of ordinary skill is lacking, guidance from the context is lacking, and where a more specific rule is not recited below, the "about" range shall be not more than 15% of the absolute value of an end point or 15% of the range recited, whichever is less.

"analyte" means a sample being analyzed, which can be a molecule in solution, in suspension, or attached to a substrate.

"backscatter" means the deflection of radiation at an angle approximately 180° to the initial direction of travel, i.e., the radiation is deflected towards the origin of the radiation. In the case of laser excited fluorescence, the back scattered radiation is directed towards the exciting laser.

"cassette" or "chemistry cassette" means a disposable device for conducting reactions therein. In one example, the cassette has a body, one or more upper membranes and one or more lower membranes which together define two or more chambers, including at least one supply chamber and one reaction chamber, and fluid exchange channels connecting the chambers; chambers of the cassette accommodate volumes that range from about 10 µl to about 500 µl.

"chamber" or "fluid chamber" is a structure for containing fluids or particular matter, which structures include any reservoir; a chamber or fluid chamber can function as the site for a reaction (hence, a "reaction chamber"), for storage of reagents (hence, a "supply chamber"), for storage of waste (hence a "waste chamber"), for volumetric metering (hence a "metering chamber"), and for storage of a sample or samples (hence a "sample storage chamber").

"channel" or "capillary" means a conduit through which fluids pass between chambers or between a chamber and an inlet or exit of a microfluidic device; also called a "fluid exchange channel".

"chip" or "microfabricated device" means a structure having chambers and at least one reaction flow way, generally accommodating substantially smaller volumes than does a cassette; for example, chambers of a chip generally accommodate volumes that range from about 0.01 µl to about 10 µl.

"connection" or "communication" between two structures selected from chambers, inlets, channels, and capillaries are said to be "connected" or have a "route of connection" or "communicate" or are in "fluid communication" therebetween if there is one or more channels or capillaries joining the two such that fluid can move from one to the other.

"fluorescence" means the emission of electromagnetic radiation, especially of visible light, stimulated in a substance by the absorption of incident radiation and persisting only as long as the stimulating radiation is continued.

"fluorophor" means a substance that fluoresces.

"location" is a site to or at which a primer, probe, target nucleic acid, or any combination thereof can be transported, attached, or held, using, for example, magnetic substrates or direct chemical bonding; such a site can be in any sort of vessel, such as the interior of a microfluidic device, or any sort of substrate, such as a microparticle.

"microfluidic device" is a device that comprises a cassette or a chip.

"moiety" is a ligand that can be attached to a substrate, such as a microparticle, that specifically binds to another ligand, thus forming a binding pair.

"probe" is a molecule that specifically binds to a second molecule, as in an antibody having specificity for an antigen or a nucleic acid being complementary to a second nucleic acid.

"reaction chamber" means a chamber for locating reactants undergoing or to undergo a reaction, comprised of any suitable material, i.e., a material that exhibits minimal non-specific absorptivity or is treated to exhibit minimal non-specific absorptivity, which material can be, for example, glass, plastic, nylon, ceramic, or combinations thereof, and is connected to at least two channels for passaging material in and out of the reaction chamber; also referred to as a "first chamber".

"reaction flow-way" means a series of two or more serially connected chambers through which fluids can move, the connections for which are provided by one or more channels or capillaries.

"serially connected" refers to two or more chambers and inlet or outlet ports that are connected via channels or capillaries by which fluid from a first of the serially connected chambers or ports can pass to a second of the serially connected chambers or ports, and from there to a third of the serially connected chambers or ports, and so on until the fluid passes to the last of the serially connected chambers or ports.

"substrate" means a surface to which a molecule can adsorb or be attached to, such as the inside surface of a microfluidic device or the external surface of a microparticle, either or both of which can include a textured material.

"target nucleic acid" or "target" means a nucleic acid having a segment that is sought to be identified, measured, or amplified in a sample, such as a sequence intended, if present, to be amplified in a nucleic acid amplification reaction such as a polymerase chain reaction (PCR) reaction or ligase chain reaction (LCR); the target nucleic acid segment is typically part of a much larger nucleic acid molecule found in the sample.

"vessel" means a receptacle in which liquid reagents can be stored or combined, ranging in volume accommodation from milliliters, with respect to wells of a microtiter dish or an Eppendorf tube, for example, 10 µl to 500 µl, with respect to fluid chambers included in cassettes, and 0.01 µl to 10 µl, with respect to such chambers in chips.

DETAILED DESCRIPTION OF THE INVENTION

The present invention is directed at the enhancement of fluorescence with respect to increasing the fluorescence yield per fluorophor. It is contemplated that one application of such increased fluorescence yield is for increasing the detection limits by fluorescence of biochemical species, such as the detection of fluorophor labeled (1) hybridized DNA or (2) antibody-antigen complexes, wherein the fluorescent detection of such species is well known for concentrations, for example, in excess of about a femtomole. Detection below that limit, and particularly substantially below that limit (for example, of a range of less than about a femtomole to about an attomole) is not currently available. The present invention renders fluorescent detection of biochemical species of amounts substantially below that limit practical.

In particular, when a fluorophor is bound to a textured material, such as, for example, a commercially available nylon or nitrocellulose membrane, fluorescence is more efficiently excited in comparison to the same fluorophor on non-textured materials or in an appropriate solution. A textured material includes surfaces that are oriented in different directions and have reflective characteristics with respect to electromagnetic radiation, such as a laser. Such textured materials provide for multiple scattering, internal reflection and interference phenomena; preferably, such materials are porous, having defined pore sizes that preclude passage of defined sizes of materials. However, such materials are not solely paper or similar fibrous materials or assemblies such as glass beads, as such fibrous or glass materials do not exhibit enhancement of fluorescence. This more efficient excitation of fluorescence is an enhanced process, and is disclosed hereinbelow with respect to the method itself and textured materials usefully employed therewith.

Preferably, commercially available fluorophors that fluoresce in the red region are used, albeit any fluorophor of any color can be used in the context of the present invention, particularly if the textured material is translucent to the excitation energy for the fluorophor. For example, a protein-based fluorophor, such as but not limited to allophycocyanin (Sigma), or an organic cyanine fluorophor, such as but not limited to indodicarbocyanine ("Cy5"; Jackson ImmunoResearch Laboratories, Inc.), are representative categories and species of dyes that show enhancement when used in accordance with the present invention. Additionally, rhodamine derivatives, such as JA22 (Niehren et al., *Anal. Chem.*, 67(15), 1 (1995)) and variants thereof, as well as variants of the aforementioned species of dyes, show enhancement when used in accordance with the present invention. This enhancement is believed to be achieved by well known processes associated with backscatter combined with or including internal reflections and local interference depending on the physical structure of the membrane.

In essence, the textured material-based fluorescence enhancement is believed to be related to unique multiple scattering, internal reflection and interference phenomena by the highly defined structure of the textured material used, such as a nylon or nitrocellulose membrane, resulting in enhancements on the order of 10 fold or more, such as 100 fold. This magnitude of enhancement is sufficiently large to support improved sensitivity and optimized formats for diagnostic assays.

Such assays can be for any suitable use, such as medical or forensic purposes, including, for example, detection of variable number tandem repeats (VNTR) as detected in Southern blots or of an antigen that is an indicator of disease or condition of a patient as detected in an immunological assay, such as an ELISA test, as known in the art. A Southern blot is a standard analytical method of molecular biology whereby DNA of an individual's genome is cut in a methodical manner, using endonucleases known to the art and commercially available, separated by size, transferred to (usually) a nitrocellulose membrane filter, the "blot" to which the DNA adheres, and probing for complementarity with short, defined sequence pieces of (usually) radiolabeled DNA ("the probe"), thereby detecting the size of the cut genomic DNA that is complementary to the probe.

The primary technical issues for the design and fabrication of an automated detection system for forensic or medical diagnostics using enhanced fluorescence are as follows:

First, the source of incident radiation for exciting the fluorescence must be calibrated with respect to backscatter configuration and laser beam width, which is preferably discussed in the context of a fluorescence detector unit. One embodiment of a fluorescence detector of the present invention is set forth in FIG. 1, wherein A is a photomultiplier (PMT), B a blocking filter, C a mirror, D a sample holder, E a sample, F a source of focused radiation, and G a shutter. This configuration measures the backscatter of the fluorophor attached to a suitable textured material, such as a nylon membrane, located at the sample (E), wherein the radiation excitation is opposite to the PMT detector A. The fluorescence directly illuminates the PMT detector A without the use of any lens, although in other embodiments, lenses can be employed. Any suitable source of focused radiation can be used to excite the fluorophor in the present method, including ultraviolet or laser sources of radiation, for example. Preferably, a laser is employed, the source of which can determine spatial resolution of the inventive method. For example, a gas laser beam diameter is on the order of 0.8 mm, whereas a solid state laser can be employed for generating various elliptical diameters, and is preferably used for a compact instrument. The beam diameter of any sort of laser can be defined by a focusing lens in these devices.

Second, quantification of the presence of fluorophor on the textured material, such as in the VNTR Southern blots, can be maximized by integration of the fluorescence associated with a particular site on the textured material, such as a region on the aforementioned blot, using conventional means.

Third, background fluorescence must be addressed and quantified. Nonspecific binding can occur with textured materials, such as nylon membranes, and the enhancement of the fluorescence can lead to high background in a hybridization assay. Accordingly, nonspecific binding of fluorophor is preferably minimized, which can be accomplished by use of standard blocking protocols. For example, one can employ a suitable detergent to inhibit non-specific absorption of fluorophor. A suitable detergent can be sodium dodecyl sulfate or polyethyllene alkyl phenylether glycols (such as polyetherylene mono(nonylphenyl)ether glycols known as Tergitol, Type NP-40); preferably Tergitol is employed.

Further, as previously noted, suitable textured materials must be identified. Such materials have microscopic pockets in and to which a first ligand can bind, which ligand binds specifically to an analyte of interest. Such ligands preferably include antibodies having immunogenic recognition of the analyte of interest or nucleic acids having a sequence complement of the analyte of interest. Suitable textured materials include, but are not limited to, nylon, poly (carbonate), poly(vinylidene difluoride) ("PVDF"), and nitrocellulose membranes. Preferably, nylon membranes are used, including commercial nylon membranes, such as those from Pall Corp. (East Hills, N.Y., or particularly, Biosupport Division, Port Washington, N.Y.), Amersham Pharmacia Biotech, Inc. (Piscataway, N.J.) and Cuno Inc. (Meriden, Conn.). There does not appear to be any substantially different enhancement variance due to pore size of the membrane. The ability to block nonspecific binding is, however, characteristic of the membrane and its manufacturer. Nonspecific binding is, as previously noted, a significant factor in the development of an enhanced fluorescent detection system.

Materials which can be inappropriate for enhancement can include many papers, bulk cottons, assemblies of glass beads and similar materials. The optical properties or the voids present in these materials can be insufficient for enhancement. Consistent with the need for multiple reflections and interference effects, materials which are too absorptive of the radiation for excitation of fluorescence also do not exhibit enhanced fluorescence. However, it is contemplated within the context of the present invention that textured materials as defined herein can be attached to glass or other beads, or a paper material, for example, which can provide for specific applications, ease of use, transport, and the like.

The present invention can be used in the context of homogeneous or kinetic assays. The enhancement in fluorescence occurs with the membrane in a solution of, e.g., Cy5 tagged amplicon, for an assay as described with respect to FIG. 2. If the membrane is pretreated with the appropriate probes, as a reverse dot blot, the binding of the Cy5 tagged amplicon will give an enhanced signal proportional to the amount of amplicon bound. If the binding is monitored with time, the kinetics of the binding event may be determined. Whether or not the kinetics is monitored, the assay will be a homogeneous assay due to the enhancement of the fluorescence by the textured material.

Hybridization or annealing conditions used in the context of any embodiment of the present invention provided for hybridization of preferably nucleic acids having preferably at least about 80% identity with respect to the length of the primer or probe and the complementary portion of a particular target nucleic acid, more preferably at least about 85% identity, yet more preferably at least about 90% identity, even more preferably at least about 95% identity and most preferably, at least about 97% identity. An example of stringent hybridization conditions is overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 $\mu$g/ml denatured, sheared salmon sperm DNA, followed by washing the hybridization support in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. One skilled in the art knows that conditions optimal for hybridization of nucleic acids having percentage identity in the range of from about 80% to about 90% identity require lesser stringency, which commonly is attained by the lessening of temperature and/or lessening of formamide concentration.

The diagnostic methods disclosed herein that use a DNA probe comprise denaturing the analyte of interest using any suitable means. Presuming that the analyte of interest is DNA, the two strands of double stranded nucleic acid (referred to herein as the "W" and "C" strands) must be separated, which can be accomplished by application of heat, enzymes, or chemicals. Preferably, a nonthermal means is used, such as by application of an enzyme from the class of enzymes known as helicases or the bacterial enzyme RecA, which has helicase activity, which in the presence of riboATP is known to denature DNA. The reaction conditions suitable for separating the strands of nucleic acids with helicases are described by Kuhn et al., in *Cold Spring Harbor Symposia on Quantitative Biology, Vol. XLIII,* 63–67 (1978); techniques for using RecA are reviewed by Radding, *Ann. Rev. Genetics,* 16, 405–437 (1982). An alternative and preferred means entails the contacting of the target nucleic acid with a suitable base such that the W and C strands of the nucleic acid separate. Suitable bases include NaOH, which preferably is used at a concentration of about 0.1 M to about 0.3 M, more preferably from about 0.1 M to about 0.2 M. Other bases can be used for chemical denaturation, as is known in the art; one of ordinary skill in the art can determine empirically what a suitable concentration is using standard techniques for any given base, which concentration can be further adjusted for any given length range of nucleic acid that is used.

The present invention can be suitably employed in the context of any vessel that includes or itself comprises a suitable textured material. For example, suitable nylon membranes, such as those prepared by the Pall Corporation, may be used in microwell titer plates for enhanced fluorescence assay wherein the bottom of the standard 96-well plate is covered with the nylon membrane. The adaptation of the various chemistries to this format, including filtering, and fluorescence detection in the plate reader format are feasible. And, as further described below, the present invention can be used in the context of a microfluidic device, wherein the textured material is placed in a channel or a chamber, and the source of radiation and PMT are assembled as set forth herein relative to the position of the textured material, i.e., the sample to be tested. Alternatively, or in addition, microparticles can be included in the microfluidic device, wherein the microparticle itself is composed of a textured material and/or a textured material is attached, directly or indirectly, to the microparticle. Other aspects of the microfluidic device are described below.

Figure 2:
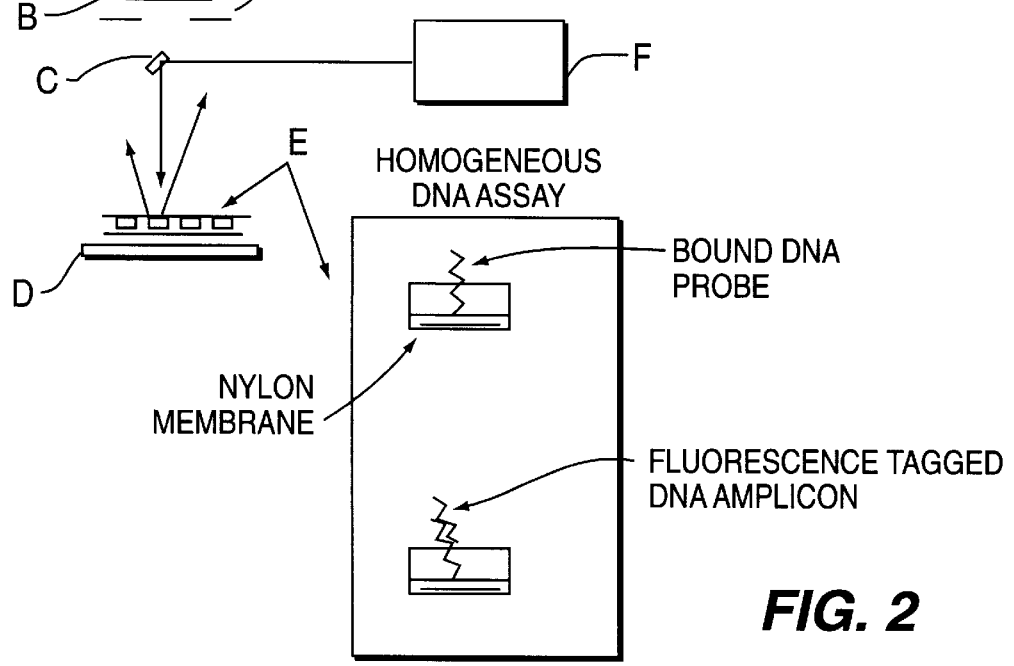
FIG. 2 displays an enhanced fluorescence unit that uses a microtiter plate for the samples.

As stated, one preferred format for instrumentation for fluorescence detection in accordance with the present invention relates to use of 96 or 384 well titer plates. A schematic of both the plate and instrument concept in accordance with this embodiment appears in FIG. 2, wherein A is a photomultiplier, B a blocking filter, C a mirror, D a sample holder, E a microwell plate having a textured material, F a laser, and G a shutter. FIG. 2 shows the general features of a DNA assay with a microwell titer plate, the wells of which include the textured material of the present invention. As shown in the enlargement of a well of the microwell plate E, the textured material can be attached to the bottom of the well, and a DNA probe can be attached to the textured material. A fluorophor-tagged DNA amplicon that is complementary to the DNA probe, using conventional conditions for hybridization, can hybridize to the probe, after which the presence or absence of fluorescence can be scored. The plate and textured material structure can have various features, such as "flow thru" for each well or a closed structure for homogeneous assays as described below. The essential feature of the concept is the use of the textured material, such as a membrane, for efficient fluorescence and the appropriate design of the plate reader for this application.

Figure 3:
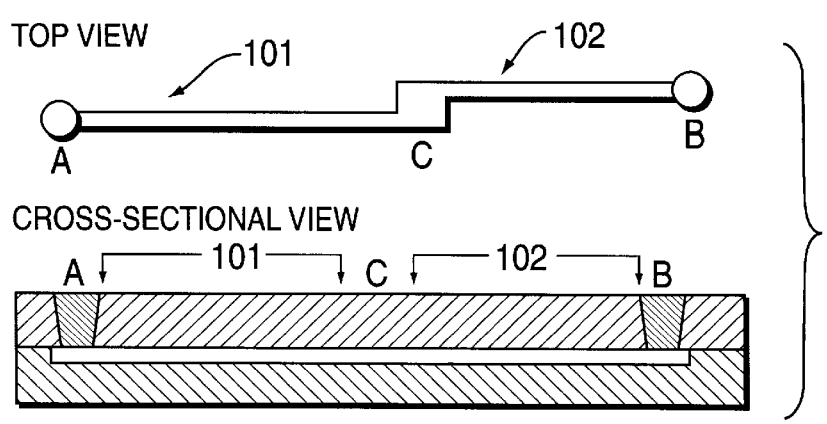
FIG. 3 depicts a microfluidic device.

In another embodiment, the present invention can be described with reference to locations to which reagents, polynucleotides, antigens, antibodies and/or substrates can be transported, which locations are generically represented as the square area in FIG. 3, for example. As noted herein, the locations so represented can have any suitable shape, including random or non-random shapes that are uniform within a particular device or not, can be a vessel of any size or shape, and multiple such locations can occupy a single area. As further noted elsewhere herein, reagents, polynucleotides, and substrates included in the aforementioned locations and used in the context of the present invention are preferably transported there between using any suitable method of transporting such substances between locations. Preferably, as further elucidated hereinbelow, the locations referred to herein are components of a microfluidic device, however, larger structures are also contemplated as being useful devices by which to operate the methods disclosed herein. Any device having separable locations will suffice. Indeed, the method of the present invention can be performed manually or automatedly using nonmicrofluidic vessels as well, such as, but not limited to, the wells of a microtiter dish, as noted above, Eppendorf tubes, and the like; or, whether a microfluidic or non-microfluidic device, the locations can be defined by magnetically positioning magnetic microparticles, for example.

As is set forth in more detail later herein, the locations noted above, as well as others as is practicable for the purpose, are preferably part of a microfluidic device. Most preferably, such a microfluidic device comprises a removable chemistry cassette or a microfabricated device, i.e., a chip. Either the cassette or chip preferably comprises a first chamber that is in communication with one or more second chambers, which chambers are designed for storage of fluid reagents or reactants, i.e., a supply chamber, for locating reactants undergoing a reaction, i.e., a reaction chamber, for measuring a volume of a fluid, i.e., a metering chamber, and more. Such chambers preferably have a volume of from about 0.001 $\mu$l to about 700 $\mu$l, more preferably from about 0.01 $\mu$l to about 500 $\mu$l, yet more preferably from about 0.01 $\mu$l to about 250 $\mu$l. The chamber is comprised of any suitable material, wherein a suitable material is selected for its ability to be molded, heated, minimize adsorption of macromolecules, and other parameters. Suitable materials include, for example, glass, plastic, ceramic, or combinations thereof. In one embodiment, a reaction chamber used in the context of the present invention is connected to at least two fluid exchange channels for passaging material in and out of the reaction chamber, which is particularly important for employing chemical means of denaturation in a diagnostic procedure. The reaction chamber preferably remains at a constant temperature of within about two degrees centigrade, wherein the temperature is between about 20° C. and 75° C. It is further preferred that the reaction chamber include the aforementioned textured material for the enhanced fluorescence method.

The location at which a probe and textured surface, such as a membrane, are located is preferably at any position in a vessel or chamber, for example. The probe is preferably an antibody or a nucleic acid, which is specific for an antigen of interest or complementary to a nucleic acid of interest, respectively. Preferably, a location is located at any interior place in the microfluidic device. Alternatively, the probe can be used in an unattached form, caused to move in the microfluidic device to a location where a particular biochemical molecule, such as an antigen or an amplicon, is located, and provide for the specific recognition via, for example, nucleic acid hybridization or immunological recognition, as appropriate, whereupon if such specific recognition occurs, the probe attaches to the particular biochemical molecule. It is further preferred that the aforementioned textured material also be located at this site of specific recognition between probe and biochemical molecule, and means be provided such that the probe, that is preferably comprised of a fluorophor, is attached at the site of specific recognition, and detected via localization of fluorescence at that site. Means for such attachment includes use of binding moieties, specifically attaching pairs of each can be used such that one moiety of a pair can be attached to the textured material and the other moiety of a pair can be attached to the probe.

Such binding moieties are used in the context of the present invention in various ways, such that, for example, binding pairs thereof can attach a substrate to a probe, wherein the substrate can include textured material. Thus, for example, the interior of a microfluidic device or the external surface of a microparticle can have attached thereto a first moiety, and a probe can have attached thereto a second moiety, such that the first moiety, for example, binds specifically or preferentially to the second moiety, thus forming a binding pair. Suitable binding pairs include, but are not limited to, (a) biotin and streptavidin, (b) an antigen and an antibody that specifically recognizes the antigen, (c) amine and hydrazide, (d) Protein A and an immunoglobulin G, (e) a carbohydrate and a lectin that recognizes the carbohydrate, (f) a nucleic acid and its complement, and the like, wherein the members of each such binding pair are referred to herein as "moieties"; thus a first moiety can be, for example, biotin and a second moiety can be streptavidin, which bind to one another but neither of which bind, for example, to a third or fourth moiety, such as amine or hydrazide, for example, which, however, bind specifically to one another. The chemical species of the binding pairs can be chemically linked directly to the respective probes or substrates or via a linking group as are known in the art; and, with respect to the surface that includes the corresponding chemical species of the binding pair that is included on a first or second primer, it too can be linked directly or by means of suitable linking groups.

Preferably, the fluorescence enhancement method of the present invention is performed in the context of a microfluidic device, preferably either a cassette or a chip, the essential difference between the two being the quantity of sample and reagents used, and the sizes of the channels and chambers included therein. In certain embodiments, a chamber functions as a reaction site, referred to herein as a "first chamber". A chamber can also function as a storage site for reagents or amplified polynucleotides, or as a waste receptacle, each of which chambers are referred to herein as a "second chamber". In certain embodiments, a particular chamber can function as a site for a reaction, thus be a first chamber, yet in another step of the method as thus embodied, the same chamber can function as a site for diagnosis of presence of an analyte of interest or a waste receptacle, thus be a second chamber.

The chambers used in a cassette or chip are one or more first chambers, in which the steps relating to the enhanced fluorescence method can take place, although the same steps can also take place in either second chambers or channels, depending on the design used in a particular embodiment. The cassette or chip used in the context of the present invention also includes at least one second chamber, which contains reagents used in the enhanced fluorescence method, or are used as a receptacle for waste that results from the enhanced fluorescence method. Again, the same second chamber that initially was a storage facility for reagents at a prior stage of the method can serve as a waste receptacle, or as a reaction chamber, or both at varying times. Simply put, the cassette and chip design provides much latitude for design variations for placement of first or second chambers and interconnecting fluid exchange channels. Valves, both of a reversible and irreversible sort, can be used in this context, including Bursapak™-type chambers that provide their own irreversible "valve." See U.S. Ser. No. 08/664,780 and PCT/US97/00298.

In this context, membrane-based hybridization may be more efficient in the microstructured device in comparison to hybridization in conventional Petri dishes. The efficiency is likely related to the fluid flow properties of these devices defined by the dimensions of these structures, e.g., as follow.

More particularly with respect to the cassette used in the context of the present invention, the cassette itself can be made of any suitable material having characteristics of sufficient moldability for forming the cassette, sufficient strength and resistance to chemical attack, and the like; for example, the cassette is preferably formed of a molded plastic, such as high density polyethylene, but other materials that are suitably resistant to the chemistries used in nucleic acid identification or amplification, such as glass and silicon-based materials, can be used. Where the cassette is formed of plastic, it is preferably formed by a molding process that is used to form cavities and channels that will be sealed with upper and lower plastic films to form chambers and fluid exchange channels, such as is illustrated in FIG. 3. Such chambers A, B and C and channels 101 and 102 are formed in suitable materials, such as glass and silicon materials, by chemical etching or laser ablation. Upper and lower films typically have a thickness of from about 0.3 mils to about 5 mils, preferably from about 1 mil to about 3 mils. For chambers having a diameter of about 1 cm or more, the film thickness is more preferably about 2 mils. The first chamber C, in which the reactions relating to the fluorescence enhancement take place in the example hereby established by example of FIG. 3, typically has a thickness, between the upper and lower films, of from about 0.1 mm to about 3 mm, preferably of from about 0.5 to about 1.0 mm, and an area, defined by the inner surface of the upper or lower films, of preferably from about 0.05 $cm^2$ to about 2 $cm^2$, more preferably from about 0.1 $cm^2$ to about 1 $cm^2$, yet more preferably about 0.5 $cm^2$. The dimensions of the first chamber are preferably sized small enough to permit rapid throughput of fluids so that the chemical conditions of the substrates having moieties attached thereto (discussed further below) can be exchanged predictably and rapidly (on the order of from about one to about 10 seconds). Preferably, the total volume of each first chamber in a cassette is between about 5 $\mu l$ and about 250 $\mu l$, more preferably, between about 10 $\mu l$ and about 100 $\mu l$. Preferably, each first chamber has a thickness (i.e., distance between upper film and lower film) of about 1 mm or less.

Fluid exchange channels in a cassette typically describe a cylinder and have a diameter between about 200 $\mu m$ and about 500 $\mu m$; alternatively, the channels can be constructed in other shapes having a width or depth respectively of from about 200 $\mu m$ to about 500 $\mu m$. Second chambers typically have a volume capacity between about 5 $\mu l$ and about 500 $\mu l$, preferably from about 10 $\mu l$ to about 200 $\mu l$, more preferably from about 30 $\mu l$ to about 160 $\mu l$. The second chambers can contain reagents required in the hybridization with enhanced fluorescence, in particular the reduction in nonspecific binding. Reagents can include the hybridization reagent, wash fluid, microparticles, Tris-EDTA (TE) buffer, and the like; such reagents can be contained in the second chambers in dry or liquid form, and if in dry form, can be constituted with water or other liquid reagent contained in other second chambers, or from water or other liquid reagent delivered from an external source. Second chambers used for metering a given volume preferably have a volume of about 5 $\mu l$ to about 50 $\mu l$.

The upper and lower films preferably are resistant to temperatures at least as high as about 120° C. and are between about 0.5 and about 4 mils in thickness, more preferably, between about 1 and about 3 mils. The thinness of the membranes facilitates rapid heat exchange between the first chamber, or wherever the reactions to be effected within the cassette are to be located, and an adjacent heating or cooling device, which can be used to establish a constant temperature for the sample of analyte being tested, if desired.

The cassette comprising the aforementioned first chambers, second chambers, including supply, waste, and metering chambers, fluid exchange channels, and the valves and pumps further discussed previously (see Ser. No. 08/664,780, for example), can have any suitable design. Indeed, any cassette design that includes at least one second chamber, at least one first chamber, and means of communication therebetween (i.e., the fluid exchange channels) suitable for the diagnosis of presence or absence of an analyte is preferred; such a design is illustrated in FIG. 3, wherein the first chamber C is in fluid communication with second chambers A and B by means of fluid exchange channels 101 and 102. More preferred, the cassette comprises up to six wells for entry of a sample container and its contents, which are connected to one or more first chambers into which the sample being amplified is distributed. The surface having the probes or analytes attached thereto can be an inside surface of the microfluidics device, such as an inside surface of a first chamber, or the surface can be microparticles as discussed above, which can be stored in second chambers.

Alternatively, the microfabricated device, i.e., the chip, used in the context of the present invention preferably includes channels or capillaries filled with fluid, wherein the channels are preferably less than about 300 $\mu m$ wide and less than about 300 $\mu m$ deep; more preferably less than about 200 $\mu m$ width and depth; yet more preferably less than about 100 $\mu m$ in width and depth. The microfabricated device can be constructed of any suitable material or combination of materials, including but not limited to glass, plastic, and the like, wherein a suitable material is substantially rigid at room temperature (about 25° C.) up to at least about 40° C., and remains a solid at a temperature of up to at least about 120° C. In addition to the channels included in the microfabricated device, a preferred device, as illustrated in FIG. 3, comprises a first chamber and one or more second chambers that are interconnected by the channels. FIG. 3 provides an illustration of a microfluidic device irrespective of size distinction between a chip and a cassette as set forth hereinabove. The first chamber is alternatively referred to as the reaction chamber, however, one of the advantages of the present method is the ability to use any chamber or any channel or portions thereof as the site of the steps needed for detecting the analyte of interest, as further discussed below. The second chambers are alternatively referred to as holding, supply or waste chambers. The aforementioned material from which the chip is constructed can vary at or about the chambers, such as, for example, including at least one deformable wall at a chamber, preferably a second chamber. Preferably, the chip has at least two second chambers that have a deformable wall.

The first chamber of a chip has dimensions, for example, of from about 1500 $\mu m$ to about 10 $\mu m$ wide, from about 1500 $\mu m$ to about 10 $\mu m$ long, and from about 5 m to about 500 $\mu m$ deep. More preferably, the first chamber has dimensions of from about 1000 $\mu m$ to about 100 $\mu m$ wide, from about 1000 $\mu m$ to about 50 $\mu m$ long, and from about 10 $\mu m$ to about 100 μm deep. Yet more preferably, the first chamber has dimensions of from about 1000 μm to about 500 μm wide, from about 1000 μm to about 70 μm long, and from about 20 μm to about 50 μm deep. The volume capacity of the first chamber of a chip is preferably from about 0.05 μl to about 50 μl; more preferably, from about 0.1 μl to about 10 μl; yet more preferably from about 0.1 μl to about 1 μl.

The second chambers have any suitable volume such that sufficient reagents and waste chambers are thereby provided in the chip for the nucleic acid amplification protocol for which the chip is designed. In most applications, volume requirements of the second chambers preferably will not exceed about 500 μl; more particularly, second chambers used for waste disposal preferably have a volume capacity of from about 200 μl to about 500 μl, whereas second chambers used for reagent storage preferably have a volume capacity of from about 50 μl to about 250 μl.

The channels included in the chip preferably have dimensions of from about 5 μm to about 500 μm wide, from about 5 μm to about 500 μm deep, and from about 500 μm to about 250 μm long. More preferably, the channels included in the chip preferably have dimensions of from about 15 μm to about 300 μm wide, from about 10 μm to about 300 μm deep, and from about 500 μm to about 100 μm long. Most preferably, the channels have dimensions of from about 30 μm to about 150 μm wide, such as, for example, 50 μm; from about 20 μm to about 100 μm deep, such as, for example, 20 μm; and from about 500 μm to about 50 μm long.

The channels can be situated colinear or not colinear with respect to the first chamber in a microfluidic device. For example, for one embodiment that has a colinear arrangement of channels and chambers, all of the channels and chambers would be aligned in the same plane as one that is parallel with the wall of the chip. In contrast, an alternative embodiment that has a non-colinear arrangement can have a chamber situated adjacent to one wall of the chip and all or some of the channels situated adjacent to the other wall of the chip, i.e., the channels or some of the channels are situated in different planes than is at least one of the chambers. In such an embodiment, the channel would connect to a chamber by a bend away from a parallel plane with the adjacent wall, bending toward the chamber. Alternatively, channels connected to a chamber can interface the chamber such that one channel can be connected to opposite corners of, for example, a square or cube shaped chamber.

In any microfluidic device, two chambers can be situated physically adjacent to each other such that they have a common orifice through which fluid communication can occur, but which, preferably, is reversibly sealed. Alternatively, the chambers can be situated physically remote from each other, which are referred to herein as "non-touching chambers", an example of which is depicted in FIG. 3, wherein the non-touching chambers are labeled A, B, and C. Preferably, non-touching chambers are in fluid communication with each other via channels or capillaries, which are labeled 101 and 102 in FIG. 3. Chambers can have any shape, including but not limited to, spheroid, cube, elliptical, and the like.

One reason that the present invention is preferably implemented in the context of a microfluidic device is that such a device includes means for translocating microparticles or reagents therein, including the probe and analytes of interest used in the context of the present invention. For example, such translocations can be effected by pumping the fluid included in the device, including, but not limited to, pumping using mechanical means, such as by means of a fluid-connected syringe wherein depressing the plunger thereof creates a positive pressure inducing movement within the microfluidic device and pulling the plunger from the barrel of the syringe creates a negative pressure inducing movement within the microfluidic device in an opposite direction. Alternative methods of moving fluids and fluid contained particulate matter in the microflouidic device includes, but is not limited to, an electrode-based pump using a conductive fluid. See Ser. No. 08/838,102, for example.

As noted above, the present invention includes the translocation of microparticles and other reagents, as well as analytes, and other reagents, as well as analytes in a chip or a cassette. A microparticle can have any shape, which is preferably spherical and, when spherical, is referred to as a "bead." Preferably, the microparticle has a length or diameter that does not exceed about 1 mm; more preferably less than about 500 μm; and yet more preferably, less than about 100 μm. In certain preferred embodiments, the microparticles have a maximum dimension of from about 0.5 μm to about 25 μm; more preferably from about 1 μm to about 10 μm; even more preferably, about 2 μm to about 5 μm. Beads used in the context of the present invention preferably have diameters that are less than the cross-sectional dimensions of channels when passage through the channels is preferred. The cross-sectional dimensions, such as the diameter of a cylinder, define the passage tolerance of a channel. Conversely, when a microparticle is preferably precluded from passage through the channels, the microparticle preferably has a diameter that exceeds at least one of the cross-sectional dimensions, i.e., the passage tolerance, of the channels, as further noted below.

Microparticles are comprised of any suitable material, the choice of material being guided by its characteristics, which preferably include minimal non-specific adsorptive characteristics, such as polystyrene. In a particularly preferred embodiment, the microparticle includes the aforementioned textured material, either as the content of the microparticle per se, or as an attachment thereto. The microparticles can be comprised of, for example, glass, cellulose or a cellulose derivative, plastic, such as nylon or polytetrafluoroethylene ("TEFLON"), metal, ceramic and the like, and combinations thereof, and preferably further comprises textured material as noted above. One skilled in the art can choose materials having the characteristic of flexibility when the preferred microparticle has a length or a diameter that approximates the cross-sectional value of the capillary or channel in which the microparticle is to be employed, wherein translocation is desirable. Such flexible microparticles, despite having a diameter that is close to the passage tolerance of a capillary or channel, or even greater than the passage tolerance, can "squeeze" through the channel when caused to move due to, for example, electrode-based pumping of fluids in the microfluidic device for translocating microparticles. Conversely, a rigid material is preferred when the microparticle is only slightly larger than the channel opening and the design of the particular chip or cassette requires that the microparticles remain in a particular reservoir.

A preferred microparticle used in the context of the present invention is magnetic or responds by being seized or manipulated by a magnetic field applied to the microfluidic device, or a portion thereof. For example, magnetic particles can be localized in a particular location of a microfluidic device, such as in a chamber, by the positioning of a magnet at a proximate position, thereby keeping the microparticles from entering a channel in fluid communication thereto.

Such magnetic microparticles can comprise the aforementioned textured material, which textured material is preferably attached to the microparticles such that the magnetic component does not quench the fluorescence process. For example, the textured material can be attached via chemical linkers so that the site of the textured material and fluorescence is removed from the site of the magnetic properties of the microparticles.

More preferably, the microparticle is paramagnetic. A paramagnetic microparticle can be comprised of, for example, iron dispersed in a polystyrene matrix, and can be obtained, for example, from Dynal (Oslo, Norway). More preferably, the microparticle is superparamagnetic as sold by Dynal (Oslo, Norway) and other commercial manufacturers. A superparamagnetic microparticle differs from a paramagnetic particle by having substantially no remanence or hysteresis. In other words, superparamagnetic microparticles respond to a magnetic field in the same fashion as paramagnetic microparticles, but whereas the paramagnetic particles exhibit some remanence and hysteresis, and therefore tend to clump together after exposure to a magnetic field ceases, superparamagnetic microparticles completely demagnetize when the field is removed, thus allowing the superparamagnetic microparticles to be redispersed without clumping immediately after the field is removed. The preferred microparticle has a moiety attached thereto. A suitable moiety provides a means for binding the microparticle to another substrate, preferably by means of a second moiety.

Another embodiment of the moiety comprises an organic or inorganic compound. Preferably, such a compound comprises an amino acid, a polypeptide, a nucleotide, a nucleoside, a nucleic acid, a carbohydrate, or an organic compound, or a combination thereof. More preferably, the moiety is a binding moiety comprising a molecule that preferentially or, yet more preferably, exclusively binds to a second molecule. Such a molecule includes, but is not limited to, avidin, biotin, streptavidin, fluorenylmethoxycarbonyl (FMOC), an antibody, a protein that binds to immunoglobulins, such as Protein A, or a lectin.

While the device is designed to allow the movement of the microparticles by pumping means, which are further discussed below, in certain embodiments and uses thereof it is preferred to hold or seize the microparticles at a certain location, or to move them as a discrete group. A preferred method for doing so includes use of magnetic microparticles, as discussed hereinabove, and requires that the device further comprise one or more magnets. Such magnets are preferably shaped and composed as disclosed in Ser. No. 08/742,971. Preferably, the magnet provides a suitable magnetic field, such as that provided by a highly magnetic permanent magnet formed of rare earths, such as those formed of the neodymium-iron-boron class of permanent magnets (available, for example, from Edmund Scientific, Barrington, N.J.). Alternatively, the magnet is an electromagnet. Either the permanent magnet or the electromagnet can be micromachined and integrated into the chip or cassette using conventional methods, as set forth by Ahn et al., *J. Microelectromech. Syst.*, 5, 151 (1996), for example.

For keeping the microparticles fixed in a given place, the passage between where the microparticles are situated and regions of the device that are in communication with that place can, for example, be narrower than the broadest dimension of the microparticles. For example, a spherical microparticle having a diameter of about 100 µm would be precluded from entering a channel having dimensions that were less than the recited diameter, particularly if the disparity of dimensions were substantial. Accordingly, a first chamber could be constructed having dimensions of 1 mm wide, 1 mm long, and 1 mm deep, containing the aforementioned spherical microparticles, and connected to channels that are substantially less than 100 µm in width and depth. By substantially less, it is preferable that the difference is at least 5%; more preferably, at least 10%; yet more preferably, at least 20%. Such a first chamber would necessarily contain the aforementioned microparticles. An alternate approach to keeping the microparticles in a fixed position requires the use of magnetic microparticles, preferably paramagnetic microparticles, more preferably superparamagnetic microparticles, and a magnet, wherein the particles are fixed at the position of the magnet. Preferably, the magnet is fixed adjacent to a reservoir, such as a first chamber, a second chamber, or a combination thereof. More preferably, the magnet is movable, such as to a location adjacent to a reservoir, such as a first chamber, a second chamber, or a combination thereof, or to a location that is not adjacent to the device. Thus, the device used in the context of the present invention has the versatility to having microparticles moved within the device or fixed in place, as per the requirements of the test for which the device is designed.

As noted above, another method of moving the microparticles or liquid reagents from position to position within the microfabricated device, is by pumping fluid within the device. Any pumping device of suitable dimensions can be used as an internal pump in the context of the microfluidics device of the invention. Such pumps can include microelectromechanical systems (MEMS), such as reported by Shoji et al., *Electronics and Communications in Japan*, Part 2, 70, 52–59 (1989) or Esashi et al., *Sensors and Actuators*, 20, 163–169 (1989) or piezo-electric pumps such as described in Moroney et al., *Proc. MEMS*, 91, 277–282 (1991). Other suitable pumps work by means of, for example, hydrodynamic pressure, as set forth by Rose and Jorgenson, Analytical Chemistry, 60, 642–648 (1988); thermal energy, as set forth by Burns et al., *Proc. Natl. Acad. Sci. U.S.A.*, 93, 5556–5561 (1996); thermopneumatic force, as set forth by Shoji and Esashi, *Journal of Micromechanics & Microengineering*, 4, 147–171 (1994); piezoelectric force, as set forth by Shoji and Esashi, supra; or electrostatic force, as set forth by Shoji and Esashi, supra, using techniques well known in the art.

Preferably, the pumps used in the present invention have no moving parts. Such pumps can comprise electrode-based pumps, which are generically referred to herein as electokinetic pumps. At least two types of such electrode-based pumping have been described, typically under the names "electrohydrodynamic pumping" (EHD) and "electroosmosis" (EO). EHD pumping has been described by Bart et al," *Sensors and Actuators*, A21–A23, 193–197 (1990) and Richter et al., *Sensors and Actuators*, A29, 159–168 (1991). EO pumps have been described by Dasgupta et al., *Anal. Chem.*, 66, 1792–1798 (1994) and Rose and Jorgenson, supra.

EO pumping is believed to take advantage of the principle that the surfaces of many solids, including quartz, glass and the like, become charged, negatively or positively, in the presence of ionic materials, such as salts, acids or bases. The charged surfaces will attract oppositely charged counter ions in solutions of suitable conductivity. The application of a voltage to such a solution results in a migration of the counter ions to the oppositely charged electrode, and moves the bulk of the fluid as well. The volume flow rate is proportional to the current, and the volume flow generated in the fluid is also proportional to the applied voltage.

Typically, in channels of capillary dimensions, the electrodes effecting flow can be spaced further apart than in EHD pumping, since the electrodes are only involved in applying force, and not, as in EHD, in creating charges on which the force will act. EO pumping is generally preferred for pumping conductive solutions.

EHD pumps are generally suitable for moving fluids of extremely low conductivity, e.g., $10^{-14}$ to $10^{-9}$ S/cm. It has been demonstrated in Ser. No. 08/730,636 that a broad range of solvents and solutions can be pumped using appropriate solutes that facilitate pumping, using appropriate electrode spacings and geometries, or using appropriate pulsed or d.c. voltages to power the electrodes.

A more preferred method of pumping uses electrosmosis. Movement of fluid within the device results from the application of an electric field to the capillary or device, wherein the capillary, reservoirs and channels through or to which the microparticles are pumped are filled with a conductive buffer. Preferably, the electric field is provided by a potential of from about 100 volts to about 30,000 volts, more preferably of from about 200 volts to about 20,000 volts, yet more preferably of from about 200 volts to about 10,000 volts, even more preferably, of from about 200 volts to about 5,000 volts, wherein the potential is applied by means of electrodes located at the outside boundaries of chambers or within channels or capillaries between which the pumping is effected. Such electrokinetic methods of pumping are further discussed in the aforementioned related applications Ser. Nos. 08/556,423 and 08/645,966.

Another preferred method of pumping is effected by a reversible actuator or roller that deforms the wall of a reservoir having a deformable wall. The hardware required to form and work such an actuator or roller are well known in the art, and is disclosed in, for example, Shoji et al., *Electronics and Communications in Japan*, Part 2, 70, 52–59 (1989) or Esashi et al., *Sensors and Actuators*, 20, 163–169 (1989).

Preferably, the present amplification method is automated, such that a controller function of a computer regulates and evaluates the process of amplification, including sensing the washing away of unbound, unincorporated matter, and assessing the accumulation of amplified product. One of ordinary skill in the software engineering art, being so instructed as by this disclosed, can prepare a suitable software program to effect these functions.

The present invention particularly relates to a method for enhancing fluorescence comprising contacting a fluorophor with a textured material, thereby forming a complex. The fluorophor preferably is any fluorescent substance; more preferably, the fluorophor fluoresces in the infrared, red, orange, or yellow region; and yet more preferably the fluorophor fluoresces in the red region. Particularly useful fluorophors include, but are not limited to, Cy5, JA22, allophycocyanin, rhodamine, fluoroscein, or a fluorophor test structurally related to one or more of the aforementioned fluorophors. The textured material has any suitable chemical composition, the suitability of which is determined by inhibiting or blocking non-specific adsorptivity of macromolecules, such as fluorescent-tagged proteins or nucleic acids, i.e., the analytes, or probes, as discussed further above. Preferred textured materials include any porous material, and are preferably formed of a polymer, such as but not limited to nylon, poly(carbonate), PUDF or nitrocellulose, of which nylon formed into a membrane is most preferred. The textured material is preferably formed by chemical, physical or biological means, such as is provided in commercially-available products such as Pall Bio-Support™ nylon membrances, Amersham nylon membranes, or Cuno Zetabind™ membranes.

Preferably, the textured material is formed randomly or orderly. Both randomly and more orderly structured textures contribute to enhanced fluorescence of the present invention. As examples, the nylon membrane products have or are formed of a disordered array of voids without well-defined structures, as achieved in microstructural devices described herein. By contrast, the poly(carbonate) membranes are formed with nearly uniform pore dimensions. Polycarbonate membranes are typically formed with nuclear tracking techniques that direct energy to create structures in the membranes, thereby creating structures that are typically more orderly than those of nylon membranes. Although these two types of membranes, as examples, have very different backscatter properties, both types exhibit enhanced fluorescence in accordance with the present invention.

A preferred embodiment of the present invention makes use of the textured material as included in or on a bead or a multi-welled plate. Particularly the bead embodiment can be used in the context of a vessel, more preferably of a chamber.

Preferably, the fluorophor is bound to a ligand, which ligand is preferably one or more of streptavidin, avidin, biotin, an antigen, an antibody specific for the antigen, a carbohydrate group, a lectin specific for the carbohydrate group, Protein A, an immunoglobulin, a nucleic acid complementary to a second nucleic acid of interest. Accordingly, the fluorophor can be bound to a substrate, such as the inside surface of a microfluidic device or the external surface of a microparticle.

The present method results in enhancement of fluorescence of about 10 fold or more relative to fluorescence of the fluorophor in the absence of the textured material. More preferably, the enhancement is at least about 50; yet more preferably, at least about 80 fold. Accordingly, the target analyte of interest can have a concentration of less than about 1 μg/ml; more preferably, of less than 100 ng/ml; yet more preferably of less than 10 ng/ml. Such enhancement and resultant sensitivities are preferably effected when the enhanced fluorescence is detected in backscatter mode. As the enhancements observed are achieved with commercial membranes which are not optimized for this phenomenon, it appears clear that enhancements in excess of those illustrated herein are achievable.

Porous membranes scatter light and the detection of fluorescence in backscatter is essential. Pitter and Jakeman (*Optics Letters*, 22 (6), 393–395 (1977)) provide recent data which confirm the enhancement of backscatter. Although the constructive interference associated with enhanced backscatter is effective in enhancing fluorescence, other optical processes, such as internal reflection in random media, can also contribute. In this context, the "void" or cylindrical structures inherent in membranes are also a factor in enhancement. Videen et al. (*Phys. Rev.*, A 43 (10), 5655–5664 (1991)) have published on fluorescence from cylinders where the cylinder diameter is comparable to the wavelength.

The present method preferably further comprises exciting the fluorophor. Such excitation of the fluorophor is preferably effected by radiation having intensity and wavelength comparable to the absorption properties of the fluorophor. Any suitable source of radiation can be used; preferably, the radiation is generated by a gas or solid state laser.

Preferably, the complex comprises a target analyte and a complementary target probe, either or both of which include the fluorophor. However, if both the target analyte and the complementary target probe include the fluorophor, then each of the target analyte and the complementary target probe include fluorophors having distinguishable fluorescence, as in exhibiting different colors upon excitation. In one embodiment of the present method, the target analyte is a first nucleic acid or an antigen, and, respectively, the complementary target probe is a second nucleic acid or an antibody, wherein the second and first nucleic acids are complementary under at least stringent hybridization conditions, and the antibody is immunologically specific for the antigen. In another preferred embodiment, the target probe or analyte further includes a binding moiety, which binding moiety comprises biotin, streptavidin, digoxigen, avidin, an antigen, an antibody specific for the antigen, a carbohydrate, a lectin specific for the carbohydrate, Protein A, or immunoglobulin G.

Preferably, the target analyte or the target probe is bound to the textured material by chemical or physical means. Such means includes the use of the aforementioned binding moieties, common covalent or ionic chemistries, or physical adsorption of a molecule to a substrate in consequence of hydrophobic, van der Waals, or other forces. For DNA binding, a preferred means includes the use of a 5' poly thymidine tail on the probe or analyte, for example, and a 3' poly adenine tail on the textured material. Other complementary oligonucleotide pairs, besides polyA/polyT, can be used. Also, one can bond DNA to nylon via ultraviolet irradiation following the work of Saiki et al., *Proc. Natl. Acad. Sci. USA*, 86, 6230–6234 (1989).

The diagnostic assays that are amenable to the present method include a kinetic assay wherein the target analyte is bound by the complementary target probe. Alternatively, the enhanced fluorescence method is used for homogenous assay. Such assays, and the enhanced fluorescence detection thereafter, preferably occurs within a microfluidic device.

Indeed, a preferred embodiment of the present invention relates to a method for identifying an analyte comprising contacting the analyte with a binding species, wherein the binding species is connected to a fluorophor that is connected to or within a textured material. Preferably, the textured material is a porous membrane, as discussed further hereinabove.

Textured Materials

The invention should not limited by the theory presented herein, as the phenomenon identified occurs with materials here identified. However, it is believed that an important characteristic for achieving the fluorescence enhancement result described herein is the presence of voids on the surface or interior of the material. It is believed that such voids provide "scatter cells" which contribute to the phenomenon, basically by increasing the pathlength of the excitatory radiate energy, thereby increasing the probability of fluorescence excitation events. It is further believed that the voids should be present in sufficient density to so that the beam of excitatory light sees a uniform density of such scatter cells.

It is further believed that the material should not absorb light of the excitatory wavelength that is to be used to induce the fluorescence. If broad band light is to be used, then the material should not be absorptive of the portion of the light that is effective to induce the fluorescence. A narrow band of light, or even laser light source, is preferred as the source of excitatory light. It is because of the absorption issue that, when nylon membranes are used, fluorescent reagents that are excited by, for example, He—Ne lasers are preferred over those excited by argon lasers.

It is further believed with many textured materials the enhancement effect is most pronounced when the emissions are collected over a relatively narrow collection surface positioned at and around an axis corresponding to the angle of reflectance for the excitatory light. Preferably, the collection surface covers no more than about the area of a 20° cone extending from the textured surface and symmetrically positioned about the above-described axis. More preferably, the collection surface covers no more than about the area of a 10° or 5° cone. Preferably, the angle of incidence of the excitatory light is substantially 90° relative to the textured surface, such that the collection zone is along the same axis, as illustrated in FIG. 1. "Substantially" 90° in this context refers to an angle which helps maintain at least about 75%, preferably at least 85%, 90% or 95%, of the fluorescence yield available with a 90° angle.

Devices

As discussed as well in the text above, the textured surfaces can be incorporated into a self-contained device for conducting reactions, such as the cassette or chip described above. Thus, such devices can be configured with the membrane at the site of an analytical reaction or at a site that receives the product of such a reaction which is to be detected. Such devices are preferably configured so that excitatory light can be directed at the incorporated textured surface and emission light collected without opening the device. Thus, the enclosing material intervening between the light source and detector and the textured material is preferably a material that is translucent in the appropriate wavelength range, such as an appropriate glass, quartz or plastic.

It has now been confirmed that textured materials such as nylon can be embossed to form structures thereon, such as reaction wells or chambers. Thus, the devices can comprise structures such as channels formed at least in part in a textured material. Where the textured material is otherwise sufficiently porous to allow fluid to travel from one side to another, one surface of the textured material can be sealed with a non-porous material.

Increased Fluorophor Gradient

Experiments have shown that applications of fluorophors to a textured surface which are designed to limit the penetration of the fluorophors into the textured surface, and which thereby increase the mass of fluorophor located in a small volume, increase the fluorescence yield from the textured surface. For example, fluorophor can be repeatedly applied in multiple small volumes (e.g., 0.1 microliter, ), with the carrier allowed to dry between each application. Alternatively, embossing, use of a thin textured material sealed on one surface or any other appropriate method can be used to assure a larger amount of fluorophor in a smaller volume of the textured material. Lateral diffusion which could limit isolation of the fluorophor in a small volume can be limited by using a textured material that is sealed onto a bead or particle, or a textured material that is sealed in a well formed of an impermeable material.

In one embodiment, the textured material is adapted to absorb the fluorophor to a depth of no greater than about 80 microns, preferably no greater than about 40, 20 or 10 microns.

Optimization

With the knowledge provided by the present disclosure, the textured material can be optimized to increase the fluorescence enhancement. For example, fabrication techniques can be varied to change the character or size or density of voids, and the changes correlated with the level of enhancement observed. As discussed above, materials can be constructed that limit the fluorophors to a smaller volume than is typically achieved with off-the-shelf materials.

Combined Liquid-Phase and Solid-Phase Assays

Since the fluorescence achieved with the invention is significantly enhanced as fluorophors become associated with the textured material, assays can be established where the increased yield can be observed with out removing non-product fluorophor, so long as the product but not the starting fluorophor associates with the textured material. Thus, assay procedures can be simplified or, for example, assays can monitored in real time to provide kinetic information or to identify an appropriate shutdown time.

Examples of such assays include hybridization assays, amplification assays (for example using a polymerase or ligase) that create an extended product which hybridizes to the textured material, ligand binding assays, and the like. Another example is an amplification assay where one product strand includes the fluorophor and the other has a member of a binding pair which is used to bond it to the textured surface; without the amplification succeeding to link the fluorophor and binding element, the fluorophor would remain in the liquid phase.

Incorporation by Reference

All publications and references, including but not limited to patents and patent applications, cited in this specification are herein incorporated by reference in their entirety as if each individual publication or reference were specifically and individually indicated to be incorporated by reference herein as being fully set forth in the text of this document. Any patent application to which this application claims priority is also incorporated by reference herein in its entirety in the manner described above for publications and references.

The following examples further illustrate the present invention, but should not be construed as in any way limiting its scope.

EXAMPLE 1

This example sets forth analytical tools for assessing the fluorescence enhancement provided by the present invention.

As described herein, membrane-enhanced fluorescence is observed for fluorophors such as Cy5 in blots on nylon membrane. The enhancement, E, is defined relative to fluorescence achieved in a standard well of a 96 well plate or an identical well in a strip of 8 wells. Comparison to the fluorescence of dried material such as streptavidin-Cy5 dried in the well of a 96 well plate or in the smaller well of a Nunc HLA plate (Terasaki Plate) has also been used. However, dried films do not form continuous layers and achieving reproducibility is very difficult. For this reason, enhancement is defined relative to a concentration of fluoropore in the volume defined by the dimensions of the exciting radiation such as the volume defined by a laser beam.

For a HeNe laser, the $1/e^2$ diameter is given as 0.08 cm. However, scattering, particularly by strepavidin may increase the width to approximately 0.1 cm. The volume for fluorescence excitation in solution and for the membrane is given in Table 1, as follows:

TABLE 1

Parameters for Evaluating E, Enhancement

| Laser Beam Diameter, cm | Solution Excitation Volume, ul | Membrane Excitation Volume, nl | E, Enhancement |
|---|---|---|---|
| 0.8 | 4.02 | 160 | 25.1 |
|  |  | 71 | 56.6 |
|  |  | 40 | 100.5 |
| 0.1 | 6.28 | 160 | 39. |
|  |  | 71 | 88. |
|  |  | 40 | 157 |

The solution volume is calculated from the diameter of the laser beam in column 1 and the height of liquid in the well, typically 8 mm for a 400 microliter volume of solution. The membrane volume is calculated from the dot blot dimension such as 2, 3 or 4 mm, the volume of sample which is generally one microliter and the area of the laser beam. The three values in column 3 correspond, respectively, to the three dot blot dimensions and the estimated volume of the sample actually excited by the laser beam. The enhancement, E, given in column 4, is the ratio of the two excitation volumes for similar fluorescence signals. In effect, the data of column 4 show that the fluorescence from the membrane requires less material than that from solution by a factor of 25–150. The process is not optimized, thus the enhancement for a given dye is at least as large as that indicated by the data, Table 1.

EXAMPLE 2

This example illustrates enhanced fluorescence of Cy5-labeled streptavidin using the method of the present invention, and provides thereby a calibration curve.

Streptavidin-conjugated Cy5 was obtained from Jackson Immunoresearch Laboratories, Inc., and diluted serially with PBS buffer (0.05 M phosphate and 0.15 M sodium chloride) so that 71, 5.68, 4.26, 2.84, 1.42 and 0.71 picograms ($10^{-12}$ grams) or about $10^{-17}$–$10^{-15}$ moles ($10^7$–$10^9$ molecules) were sequentially placed on a nylon membrane (Biodyne A™, 0.45 micron) purchased from Pall BioSupportDiv., Pall Corporation as nominal 2 mm dot blots using 1 microliter of solution. A fluorescent signal was detected in the so treated nylon membrane using the backscatter method. The backscatter method refers to collection of fluorescent light on the same side of the membrane as that of the laser excitation. The fluorescence signal, corrected for background, is given in Table 2 for each of the above listed amounts of streptavidin-Cy5.

TABLE 2

| Grams × $10^{-12}$ | Counts per sec |
|---|---|
| 71 | 6425 |
| 5.68 | 440 |
| 4.26 | 350 |
| 2.84 | 205 |
| 1.42 | 145 |
| 0.71 | 40 |

Figure 4:
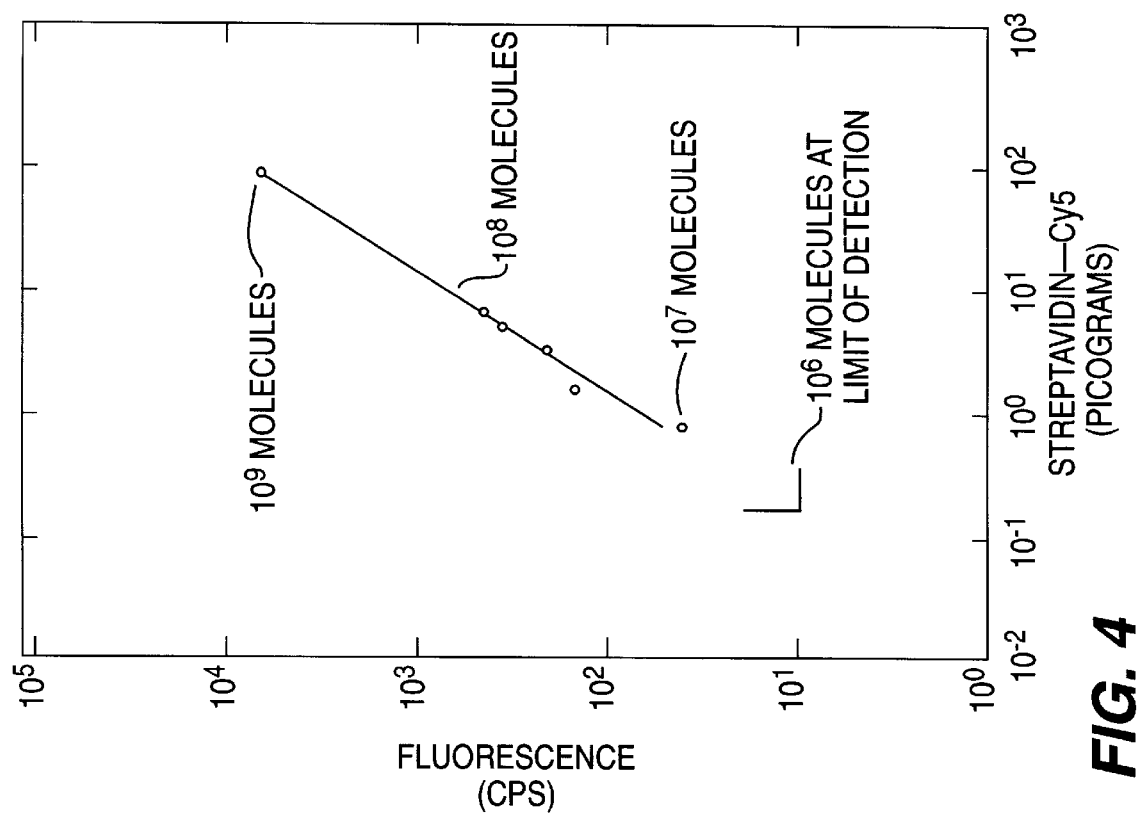
FIG. 4 is a calibration graph that displays Fluorescence (cps) vs. Streptavidin-Cy5 (picograms).

These data are shown in FIG. 4, which is a graph of fluorescence signal in counts per second (y axis) and the weight of streptavidin-Cy5 in picograms (x axis). The data indicate that about $10^7$ molecules result in less than 100 cps and $10^6$ molecules is the current limit of detection resulting in about 10 cps of fluorescence for an unoptimized detection system. Other data points not included show that the relation between fluorescence signal and the weight of the same material is linear for higher concentrations, up to micrograms. Higher weights than micrograms were not studied.

Figure 5:
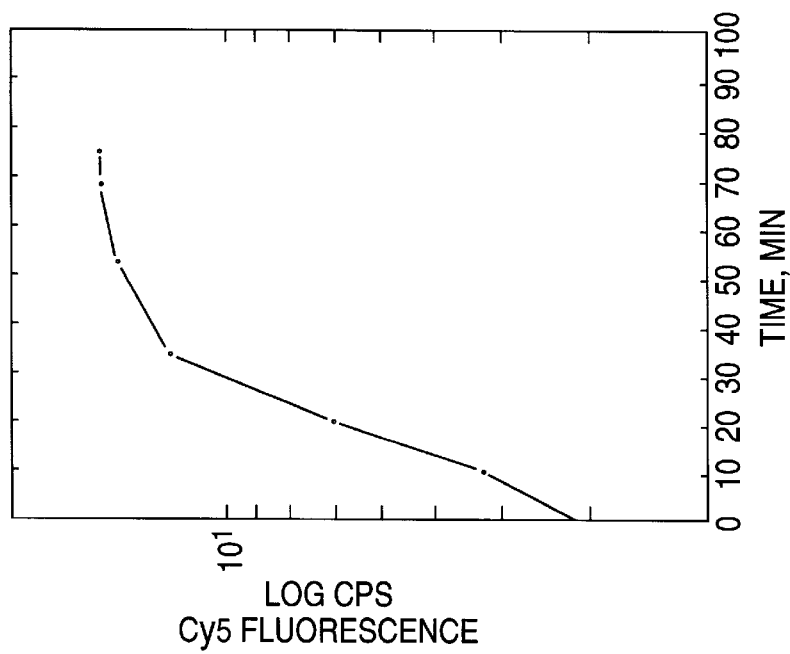
FIG. 5 is a graph that displays Fluorescence (log cps) vs. Time (min).

The data, Table 2, and FIG. 5, represent Cy5 without system optimization. Other dyes exhibit similar or greater fluorescence and the data given are only an example.

EXAMPLE 3

This example illustrates one embodiment of the method to enhance fluorescence and detection of same. A single dot blot is used to demonstrate the use of enhanced fluorescence for a homogeneous or kinetic assay. A dot blot was prepared by applying 1.0 microliter aliquots of a 1316 microgram/milliliter stock of probe DNA specific for beta-globin amplicons, i.e., 148696 picomoles/milliliter (Molecular Weight, 8853D) onto a Pall BioSupport membrane (Biodyne A). The stock was obtained from Research Genetics (Huntsville, Ala.). The resultant dot blot on the membrane was 2–3 mm in diameter. A laser beam from a diode laser (LaserMax MDL-200-635-5) emitting at 635 nm, having a focused beam of about 1 mm, was used; thus the laser beam irradiates the dot blot continuously in a cell whereby the membrane is exposed to a solution containing the beta-globin amplicon. The beta-globin amplicon was prepared by the procedures given by Wu et al., Proc. Natl. Acad. Sci. USA 86, 2757–2760 (1989) or procedures made available by Perkin Elmer (Applied Bioscience Div.) with primers which were synthesized with Cy5 on one of the primers (Research Genetics). Thus the amplicon fluoresces when excited by the laser light. On initial exposure to the amplicon solution in a 1 mm cell, the fluorescence signal was 3,100 cps representing the combined effects of solution and membrane fluorescence. This also represents the starting conditions for a homogeneous binding assay.

With time, hybridization, although not optimized, occurred. The data obtained are given in Table 3, as follows:

TABLE 3

| Time, min | Cy5 Fluorescence Signal, cps |
|---|---|
| 0 | 3,100 |
| 10 | 4,250 |
| 20 | 7,000 |
| 33 | 12,000 |
| 52 | 14,000 |
| 68 | 15,000 |
| 74 | 15,000 |

These data are given in FIG. 5 which suggests the log of the signal is linearly related to time; the relation between the log of the signal and time may be interpreted in terms of a kinetic process as a characteristic of this particular homogeneous assay. More generally, these data show the following:

(1) without regard to the time of the assay, a homogeneous assay is feasible wherein the binding to the membrane gives a signal to 15,000 cps whereas in the absence of binding to the membrane and from the solution only gives a signal of 3,100 cps. The homogeneous assay can be based on the 5-fold increase in fluorescence due to the fluorophor containing probe binding to the membrane.

(2) with regard to the time of the assay, a kinetic assay is feasible wherein the binding to the membrane is measured as a function of time. The 5-fold increase in fluorescence establishes a strong signal which may be used to measure hybridization rates for array assays using arrays of probes.

EXAMPLE 4

This example illustrates the use of the method of enhanced fluorescence and detection of DNA amplicons that are complementary to the β-globin gene within microstructured devices. The use of a membrane material in these structures provides of efficient hybridization and fluorescence detection in comparison to conventional methods such as those involving Petri dishes.

For this example, a plastic, molded cassette of a structure previously described at U.S. Ser. No. 08/664,780 and PCT/US97/00298, for example was modified to retain a Pall BioSupport (Pall Co.) membrane (Biodyne A) within one chamber. The chamber dimensions are a nominal 1 cm in length and 5 mm in width with a height of about 75–150 microns. The membrane was cut to dimensions to fit within the chamber. A dot blot was prepared by applying 1.0 microliter of a 45.4 picomoles/microgram stock of probe DNA, designated NGP Poly T, having the following sequence 5'-TGA-CTC-CTG-AGG-AGA-AGT-TTT-TTT-TTT-TTT-TTT-3'  [SEQ ID No: 1].

NGP Poly T is specific for beta-globin amplicons (Molecular Weight, 10159D) and was used on a Pall BioSupport membrane (Biodyne A). The probe was synthesized by Research Genetics with a short poly(T) tail for UV binding to the nylon membrane following the procedures of Saiki et al., supra. The resultant dot blot on the membrane was 2–3 mm in diameter. Two additional dot blots were also prepared as controls, one as a blank and the second with a well characterized, universal HLA probe, DB344, which is disclosed in Buawan et al., Tissue Antigens 44, 137–147 (1994). This probe, also synthesized with a short Poly (T) tail, was used to test the specificity of the hybridization. A blocking solution prepared from dried fat-free (skimmed) milk was used prior to hybridization, in accordance with standard procedures. Sambrook et al. As stated above, detergent may also be used, preferably Tergitol NP-40. Cy5 fluorescence was measured to determine the hybridization of the β-globin amplicon to the NGP Poly T probe. The β-globin gene was included in DNA isolated from human white blood cells, and a polymerase chain reaction (PCR) using a standard protocol was run using one or both of the Cy5 tagged primers identified as GH20 and PC04 by Perkin Elmer:

Primer 1, GH20: 5'-GAA-GAG-CCA-AGG-ACA-GGT-AC-3'  [SEQ ID No: 2]

Primer 2, PC04: 5'-GGT-GAA-CGT-GGA-TGA-AGT-TG-3'  [SEQ ID No: 3]

The Cy5 is synthesized onto the primer at the 5' end unless otherwise specified (Research Genetics).

Using the method and instrumentation set forth in Example 2, a signal of 22,146 counts per second (cps) of fluorescence trapped on the Pall Biodyne A nylon membrane was measured. The blot defined as a blank (control) and that defined with the HLA 344 probe exhibited 9,350 and 10,827 cps respectively and the ratio of signal (amplicon) to background is 2.4. Subsequent optimization of the blocking gave a signal to blank background ratio of approximately 30, i.e., very low background. These data demonstrated the capability of using a membrane within a cassette or microfluidic structure and, by flow of reagents such a buffers and amplicon, obtaining an enhanced fluorescence signal, here approximately a microgram of amplicon, for DNA detection.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A device for conducting reactions comprising:

an assay device comprising a detection or reaction chamber which contains a textured material that enhances fluorescence of a fluorophor associated therewith, the association of the textured material with the fluorophor providing at least a 10-fold enhancement in fluorescence yield of the fluorophor, wherein the textured material comprises voids or pores effective to create backscatter of the fluorescence exciting light;

a source of light selected to emit light that is not absorbed by the textured material in an amount effective to diminish the fluorescence enhancement, which light source is aligned with at least one detection or reaction chamber, wherein the light source directs light at an angle sufficiently close to a 90° angle relative to the textured surface so that the fluorescence yield is at least 75% of that available with a 90° angle; and a detector aligned to collect emissions located within a 20° cone surrounding the axis of reflection of the light emitted by the light source.

2. The device of claim 1, wherein the the textured material is a porous membrane that is formed of nylon, poly(carbonate) or nitrocellulose.

3. The device of claim 1, wherein association of the fluorophor and textured material yield at least a 50-fold enhancement in the fluorescence yield of the fluorophor.

4. The device of claim 1, wherein the light source is a source of coherent light.

5. The device of claim 1, wherein the detector is aligned to collect emissions located within no more than a 10° cone surrounding the axis of reflection of the light emitted by the light source.

6. The device of claim 1, wherein the detector is aligned to collect emissions located within no more than a 5° cone surrounding the axis of reflection of the light emitted by the light source.

7. The device of claim 1, wherein the light source directs light at an angle effective to yield at least 85% of the fluorescence yield available using a 90° angle relative to the textured surface.

8. The device of claim 7, wherein the textured material is a porous membrane that is formed of nylon, poly(carbonate) or nitrocellulose.

9. The device of claim 1, wherein the light source directs light at an angle effective to yield at least 90% of the fluorescence yield available using a 90° angle relative to the textured surface.

10. The device of claim 1, wherein the light source directs light at an angle effective to yield at least 95% of the fluorescence yield available using a 90° angle relative to the textured surface.

11. The device of claim 1, wherein the light source directs light at a 90° angle relative to the textured surface.

12. A device for conducting a fluorescence measurement comprising an textured material, which textured material enhances the fluorescence of a fluorophor associated therewith providing at least a 10-fold enhancement in the fluorescence yield of the fluorophor when detected in backscatter mode, embossed to define a reaction well or chamber, wherein the textured material comprises voids or pores effective to create backscatter of the fluorescence exciting light.

13. The device of claim 8, wherein the embossed, textured material is sealed on the opposing side to prevent fluid transit therethrough.

* * * * *

SEQUENCE LISTING

<160> NUMBER OF SEQ ID NOS: 3

<210> SEQ ID NO 1
<211> LENGTH: 33
<212> TYPE: DNA
<213> ORGANISM: Unknown
<220> FEATURE:
<223> OTHER INFORMATION: Unknown Organism

<400> SEQUENCE: 1
tgactcctga ggagaagttt tttttttttt ttt                    33

<210> SEQ ID NO 2
<211> LENGTH: 20
<212> TYPE: DNA
<213> ORGANISM: Unknown
<220> FEATURE:
<223> OTHER INFORMATION: Unknown Organism

<400> SEQUENCE: 2
gaagagccaa ggacaggtac                                   20

<210> SEQ ID NO 3
<211> LENGTH: 20
<212> TYPE: DNA
<213> ORGANISM: Unknown
<220> FEATURE:
<223> OTHER INFORMATION: Unknown Organism

<400> SEQUENCE: 3
ggtgaacgtg gatgaagttg                                   20